(12) United States Patent
Hess

(10) Patent No.: US 6,233,488 B1
(45) Date of Patent: May 15, 2001

(54) SPINAL CORD STIMULATION AS A TREATMENT FOR ADDICTION TO NICOTINE AND OTHER CHEMICAL SUBSTANCES

(76) Inventor: Carl A. Hess, 23772 Medinah La., Laguna Niguel, CA (US) 92677

( * ) Notice: Subject to any disclaimer, the term of this patent is extended or adjusted under 35 U.S.C. 154(b) by 0 days.

(21) Appl. No.: 09/344,833

(22) Filed: Jun. 25, 1999

(51) Int. Cl.[7] .................................................. A61N 1/32
(52) U.S. Cl. ............................................. 607/58; 607/117
(58) Field of Search .............................. 607/58, 43, 117

(56) References Cited

U.S. PATENT DOCUMENTS 5,370,672 * 12/1994 Fowler et al. ........................ 607/58
5,417,719 * 5/1995 Hull et al. ............................ 607/46
5,458,625 * 10/1995 Kendall ................................ 607/46
5,733,322 * 3/1998 Starkebaum ....................... 607/117
5,776,170 * 7/1998 MacDonald et al. ................ 607/46

* cited by examiner

Primary Examiner—Carl H. Layno
(74) Attorney, Agent, or Firm—Morgan & Finnegan, LLP (57) ABSTRACT

A new method for suppressing chemical substance craving comprises an electrical stimulation of the spinal cord using one or more implantable leads containing at least two conducting electrodes. The method may be used to suppress craving for alcohol, narcotics, cocaine, and amphetamines. The method is particularly suited to the suppression of nicotine craving.

57 Claims, 7 Drawing Sheets

SPINAL CORD STIMULATION AS A TREATMENT FOR ADDICTION TO NICOTINE AND OTHER CHEMICAL SUBSTANCES

BACKGROUND OF THE INVENTION

The present invention relates to a new method for suppressing chemical substance craving comprising electrical stimulation of the spinal cord using one or more implantable leads containing at least two conducting electrodes. The method may be used to suppress craving for alcohol, narcotics, cocaine and amphetamines. The method is particularly suited to the suppression of nicotine craving.

Tobacco related deaths are the largest single cause of premature death in developed countries. More than 400,000 deaths per year are linked to smoking related illness in the U.S. alone. However, despite the well publicized risks and consequences associated with tobacco use, more than 25% of adults in the United States continue to smoke with prevalence rates varying according to demographics.

The benefits of smoking cessation are substantial. Immediate benefits accrue to smokers who quit, including those with smoking-related disease. The risk of disease declines with smoking cessation and continues to drop through periods of abstinence. After 10–15 years of abstinence, mortality risks are equal to those of non-smokers. Smoking cessation decreases the risk of stroke, aortic aneurysm, peripheral vascular disease and myocardial reinfarction in individuals with myocardial infarction. Similar risk reduction exists in the incidence of smoking related cancers, chronic obstructive pulmonary disease and pregnancy related complications. An effective treatment for smoking addiction would result in a significant public health advance.

Previous attempts to effect smoking cessation can be divided into two categories, non-pharmacologic interventions and pharmacologic interventions. Non-pharmacologic interventions focus on altering the behavioral conditioning of smokers so that smoking is avoided or is a disfavored activity. Pharmacologic interventions are geared toward lessening the craving for nicotine and are divided into the current mainstay, nicotine replacement therapy (the only pharmacologic therapy with FDA approval) and other forms of drug therapy. The patented pharmacologic therapies employ transdermal azapirones (U.S. Pat. Nos. 5,837,280; 5,817,679; 5,633,009), nicotine receptor agonists and antagonists (U.S. Pat. Nos. 5,817,331; 5,691,365), nicotine lozenge (U.S. Pat. Nos. 5,662,920; 5,549,906), cotinine (U.S. Pat. No. 5,612,357), transdermal nicotine systems including subsaturated prolonged activity patches (U.S. Pat. Nos. 5,004,610; 4,839,174), and methods for anticholinergic blockage of withdrawal symptoms (U.S. Pat. No. 4,555,397). Unfortunately, as discussed below, none of the varied therapies, whether used singly or in combination, are very effective.

The effectiveness of various methods for smoking cessation was studied and reported in a large meta-analysis derived from 188 randomized controlled trials evaluating multiple interventions intended for smoking cessation (See Law, M. An Analysis of the Effectiveness of Interventions Intended to Help People Stop Smoking. *Archives Internal Medicine.* 1995; 155:1933–1941). In the meta-analysis, previously investigated interventions were evaluated and their outcomes given.

The meta-analysis found that even the most effective therapies (nicotine replacement) showed a marginal success rate of 13%. No other therapy or therapies in combination showed success rates of greater than 5% except in the rare instance of special risk groups (pregnant women, patients with ischemic heart disease or previous myocardial infarction) who exhibited up to an 8% quit rate when given advice and encouragement to quit based on their special risk. Non-pharmacologic therapies fared poorly with the success rates no greater than that achieved with physician advice. More recently, a Mar. 2, 1999 *New York Times* article indicated new success using a combination therapy with sustained buproprion, nicotine replacement and counseling, citing an Oct. 23, 1997 article in the *New England Journal of Medicine* (Vol. 337, No. 17, pg. 1195). However, despite initial promise, one year follow-up cessation rates were 24.4% at the highest buproprion dose compared to 10.5% cessation rate for placebo. This rate advantage over placebo was consistent with the poor success rate using other methods. These low success rates illustrate the limitations and failures of the prior interventions and highlight the need for improved treatments to effect smoking cessation.

Clearly, there exists a real need in the art for effective therapies and specifically more effective non-pharmacologic therapies in the treatment of nicotine addiction. There is also a need in the art to develop non-pharmacologic therapies for the treatment of addictions to other chemical substances such as alcohol, narcotics, cocaine and amphetamines.

SUMMARY OF THE INVENTION

The present invention relates to a method for treating addiction to nicotine and other chemical substances comprising electrical stimulation of the spinal cord or nervous system of the patient using one or more commercially available implantable spinal cord stimulation leads for a time period sufficient to suppress or extinguish the nicotine craving of the patient. The inventive method may be used either alone or in combination with drug or behavioral therapies.

The effectiveness of the inventive method is believed to be related to the presence of nicotine receptors in the spinal cord which can be activated by spinal cord stimulation. Receptor and receptor systems, nerve and nerve endings of varying size, and neurotransmitters are distributed at all levels in the spinal cord. In particular, nicotine receptors are found in the central nervous system (brain and spinal cord) and analgesia is produced by nicotine both systemically and in the spinal cord. Potential mechanisms proposed for the production of analgesia by spinal cord stimulation suggest that stimulation of the dorsal horn of the spinal cord activates endogenous inhibitory systems which can modulate or block the sensation of pain. These inhibitory systems include, but are not limited to, endorphin and enkephalin systems (opiate systems), serotonergic, adenosingergic, adrenergic, dopinamergic and finally cholinergic systems. Nicotine receptors are found within the cholinergic system. Stimulation of the cholinergic (inhibitory) systems in the spinal cord produces antinociception (pain relief). Therefore, stimulation of the cholinergic and thereby the nicotinic system in the spinal cord should also mimic the presence of nicotine by activating the nicotinic receptors, but by a non-pharmacologic method. Thus, stimulation of the nicotinic system should mimic nicotine both systemically and locally in the central nervous system. As a net result of this stimulation, a patient treated with spinal cord stimulation should experience decreased craving for nicotine and an ability to interrupt behavioral components thereby allowing the patient to overcome the addiction.

The inventive method uses one or more implantable leads which are comprised of a plurality of conducting electrodes adapted for accurate placement within the human body, in particular the area of the spinal cord or nervous system to be stimulated. Various devices for spinal cord stimulation used in chronic pain management and movement disorders are disclosed in U.S. Pat. Nos. 3,654,933, 4,044,77, 4,379,462, 5,058,584, 5,417,719, 5,501,703 and 5,643,330 which are all herein incorporated by reference in their entirety.

The method described is also applicable to the treatment of addiction to alcohol, narcotics, cocaine. amphetamines and other chemical substances since receptor systems (e.g. opiate receptors for narcotics) specific for these substances are also found in the spinal cord.

In clinical practice, the suitability of the inventive method for a particular patient is determined by first screening the patient using various psychological criteria to determine if he is a suitable candidate for the procedure. If the patient passes the screening procedure, a trial implantation and stimulation is carried out. The results of the trial are then evaluated. If the patient demonstrates successful suppression or extinction of nicotine craving as a result of the implantation and stimulation, the lead or leads are then permanently implanted in the patient.

DETAILED DESCRIPTION OF THE INVENTION

The basic elements needed for the method and application of spinal cord stimulation for suppression of chemical substance craving, in particular, nicotine, comprise a spinal cord stimulator lead and a power source connected to the lead to enable conduction of electrical impulses to the spinal cord. The spinal cord stimulator lead contains external contact electrodes at the distal tip which send impulses into the spinal cord. These distal contact electrodes are independently connected to corresponding contact terminals at the proximal end of the lead by separate stranded wires which run substantially parallel to each other. The proximal conductive terminals are in turn connected to an electrical power source through a lead extension connector which makes individual contact with the proximal lead terminals and allows transmission of electrical signals from the power source to the distal lead electrodes. The generator or electrical source provides electrical stimulation and allows for the selective and independent variation of characteristics of the electrical power including amplitude, frequency rate (heretofore referred to as "rate") and pulse width, as well as variation in the polarity of the conducting electrode contacts within the lead (any number of lead contacts from four to eight to sixteen in current technology). If technologically feasible, in an alternative embodiment, the lead extension connector may be omitted and the electrical power source connected directly to the proximal conductive terminals.

The amplitude of the electrical power may be varied between about zero volts to about fifteen volts and is chosen to be as high as can be tolerated by the patient so as to achieve maximum stimulation. Preferably, the voltage is varied between about 0.1 volts to about eight volts. More preferably, the voltage is varied between about zero volts to about six volts and most preferably, the voltage is varied between about zero to about four volts. The pulse width of the electrical power may also be varied at the same time as one or more of the characteristics of the electrical power or may be separately varied with the other characteristics held constant. Preferably, the pulse width is varied between about zero to about 450 microseconds. More preferably, the pulse width is varied between about 180 to about 270 microseconds and most preferably, the pulse width is varied between about 240 to about 270 microseconds. The rate of the electrical power may also be varied at the same time as one or more of the characteristics of the electrical power or may be separately varied with the other characteristics held constant. Preferably, the rate is varied between about zero to about 150 cps. More preferably, the rate is varied between about 25 to about 80 cps and most preferably, the rate is varied between about 50 to about 80 cps.

The number of leads implanted ranges from one lead to ten leads. Preferably, the number of leads implanted ranges from one lead to four leads. More preferably, the number of leads implanted ranges from one lead to two leads. Most preferably, the number of leads implanted is two.

Preferably, the lead or leads are inserted into the epidural space of the spinal cord and contact the external portion of the dura to stimulate the neural structures underneath. The lead or leads may be inserted into the sacral, caudal, lumbar, thoracic or cervical spines. The position of the implanted lead or leads ranges from the sacral position to the high cervical position of the spinal cord. Preferably, the lead or leads are implanted from the upper lumbar to the lower cervical position in the spinal cord. More preferably, the lead or leads are implanted from the lower thoracic to the higher thoracic position of the spinal cord. Most preferably, the lead or leads are implanted from the lower thoracic to the middle thoracic position in the spinal cord. The lead or leads are positioned so that the lead or leads are parallel to the midline of the spinal cord and may be positioned to the right of the midline, directly on the midline or to the left of the midline. The lead or leads may also be placed oblique or transverse to the midline. If more than one lead is implanted, the leads may be positioned both to the right and left of the midline of the spinal cord.

All lead contacts and conductors are electrically insulated by a suitable insulating material which is safe for implantation in the human body. The distal contact electrodes may have variable contact surface area as well as variable spacing between electrodes. The number of electrodes may be varied as well. Current technology allows a total of 16 electrodes to receive electrical transmission from a single energy source. For example, four quadripolar (four electrode) leads may be connected to a single power source or two eight electrode leads may be connected to a single power source. The number of electrodes per lead ranges from between at least two to sixteen electrodes per lead. Preferably, the number of electrodes per lead ranges from between four to eight per lead. Most preferably, the number of electrodes per lead is four. If multiple leads are implanted, the number of electrodes per lead may be the same or different.

Electrode polarity refers to activation of lead electrodes by assigning positive or negative charge to the electrode. Polarity can include as few as two electrodes per lead (one positive, one negative) on up to as many electrodes as are contained on the lead (with at least one electrode positive and at least one electrode negative). Systematic electrode polarity assignments are made during trial stimulation beginning with the second and third most distal electrodes (in a four electrode system) as postive and negative respectively. Additional electrodes are added or substituted to improve coverage area and maximize stimulation. The lead or leads are positioned so that optimum stimulation occurs without using the most distal/proximal electrodes which allows these electrodes to be used in the event of lead migration (i.e., these electrodes can be activated if the lead moves up or down the spine respectively).

Variation in the polarity of the electrodes is achieved by activating at least two electrodes per lead up to the maximum number of electrodes contained on the lead. Preferably, the number of electrodes activated per lead ranges from at least two up to eight electrodes per lead. More preferably, the number of electrodes activated per lead ranges from at least two up to four electrodes per lead. Most preferably, three electrodes are activated per lead.

Lead electrode systems may be percutaneous as described in U.S. Pat. No. 4,004,774 or wider (paddle) systems may be inserted surgically through a laminotomy or laminectomy incision as described in U.S. Pat. Nos. 3,822,708, and 3,654,933 which are hereby incorporated by reference in their entirety. If multiple leads are implanted, they may be inserted at the same or different levels and used for more complete stimulation coverage.

Examples of totally external power systems include those systems which are used for temporary trial stimulation. Internally implanted systems include totally implanted generators or can include implanted receivers which are internalized but which receive input from an external power source transmitted through antennae. The external systems are radiofrequency power sources which may be used for patients with higher energy requirements.

Figure 1A:
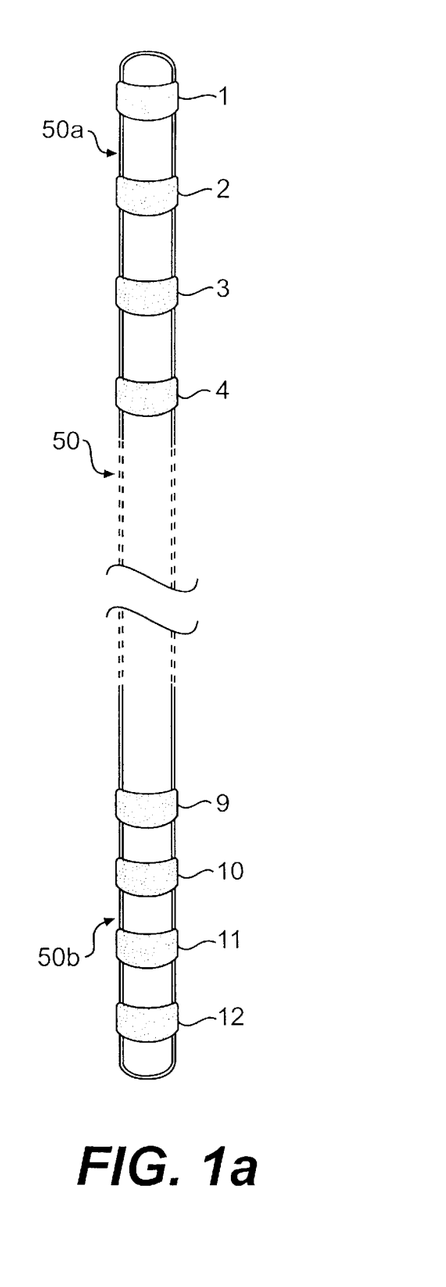
FIGS. 1a, 1b and 1c illustrate a 4-electrode, an 8-electrode percutaneous lead and a surgically implanted lead respectively suitable for use in the inventive method.
Figure 1B:
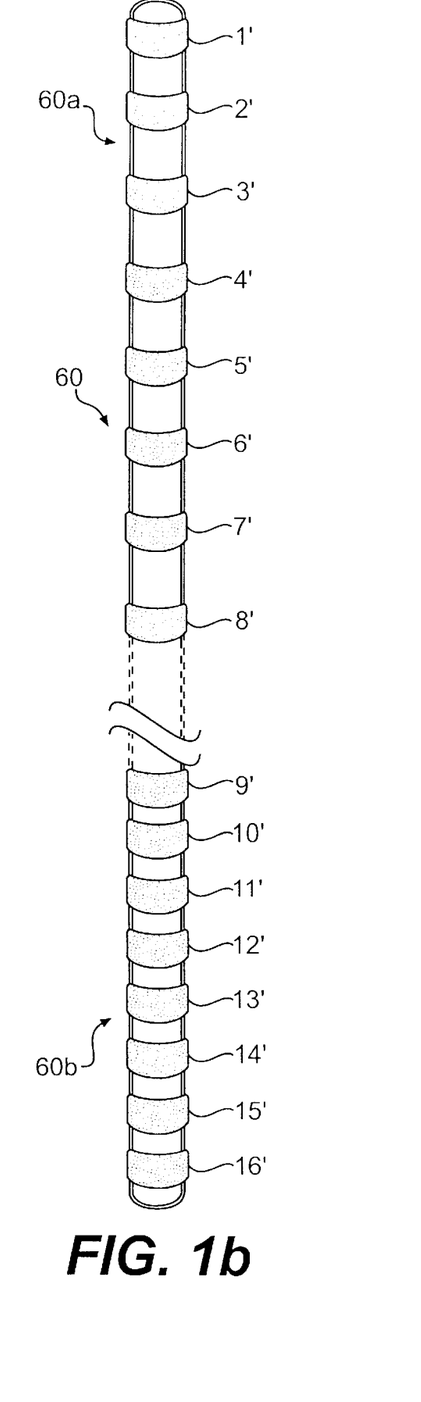
Figure 1C:
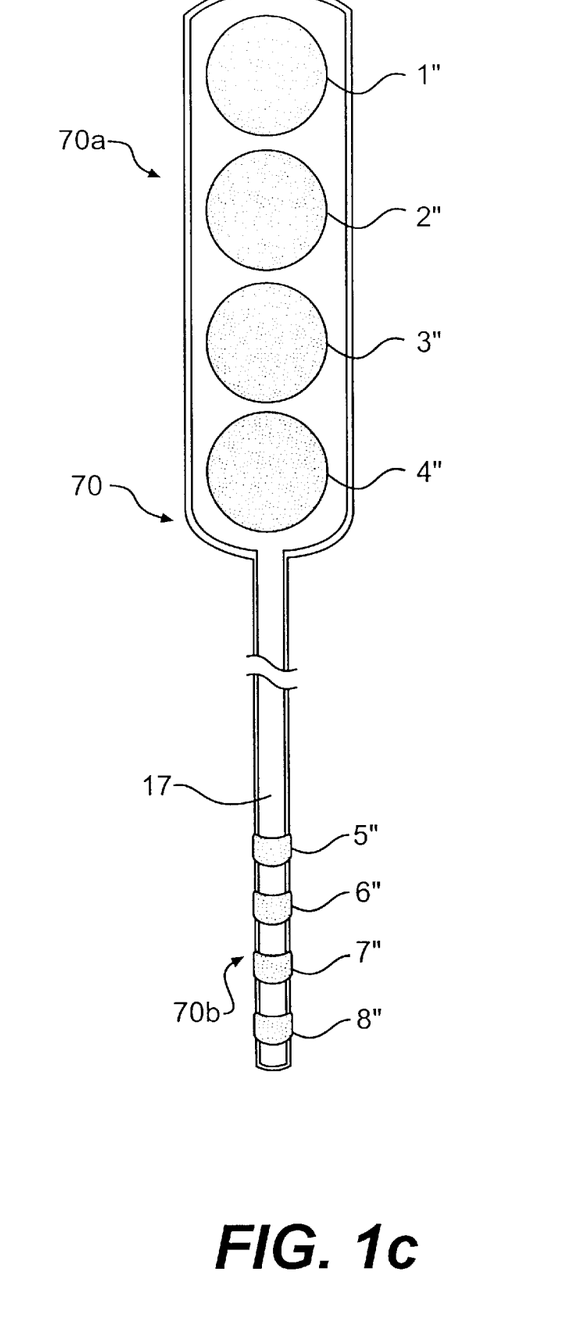

FIG. 1 illustrates three different leads, a four-electrode percutaneous lead 50 (FIG. 1*a*), an eight-electrode percutaneous lead 60 (FIG. 1*b*) and a surgically implanted lead 70 (FIG. 1*c*). Four-electrode lead 50 comprises an insulated tube with a distal end 50*a* and a proximal end 50*b* with four external conducting electrodes at the distal end 50*a* as previously described. A first external conducting electrode 1 is positioned most distal on the lead (closest to the distal tip). A second external conducting electrode 2 is positioned a given distance proximally from external conducting electrode 1. A third conducting electrode 3 and a fourth conducting electrode 4 are respectively spaced at given distances proximal to electrode 2. The eight electrode lead 60 comprises a distal end 60*a* and a proximal end 60*b*. The lead 60 further comprises external conducting electrodes 1', 2', 3', 4' at the distal end 60*a* as described for lead 50 above and additionally comprises a fifth conducting electrode 5', a sixth conducting electrode 6', a seventh conducting electrode 7' and an eighth conducting electrode 8' as illustrated in FIG. 1*b*. In the surgical lead 70, the lead comprises a distal end 70*a* and a proximal end 70*b*. The lead 70 illustrated in FIG. 1*c* further comprises disc-shaped external conducting electrodes 1", 2", 3" and 4" at the distal end 70*a*. These electrodes are of greater size and have a larger conduction surface than the comparable structures in the percutaneous leads depicted in FIGS. 1*a* and 1*b*.

The proximal end 50*b* of lead 50 comprises tube-conducting terminal connections, 9, 10, 11 and 12 which are connected by individually stranded wire running substantially parallel but separately. 9, 10, 11 and 12 extend to and are in contact with external conducting electrodes 1, 2, 3 and 4 respectively. The proximal end 60*b* of lead 60 comprises tube-conducting terminal connections 9', 10', 11', 12' and additionally comprises tube-conducting connecting terminal connections 13', 14', 15' and 16' which are connected by individual separate stranded wires to external conducting electrodes 1', 2', 3', 4', 5', 6', 7' and 8' respectively. The proximal end 70*b* of surgical lead 70 comprises tube conducting terminal connections 5", 6", 7" and 8" which are connected by individual separate stranded wires to external conducting electrodes 1", 2", 3" and 4" respectively. An insulating material 17 is interposed between each of the conductors on all three leads 50, 60 and 70 and exists throughout the lead.

Figures 2A, 2B, 2C:
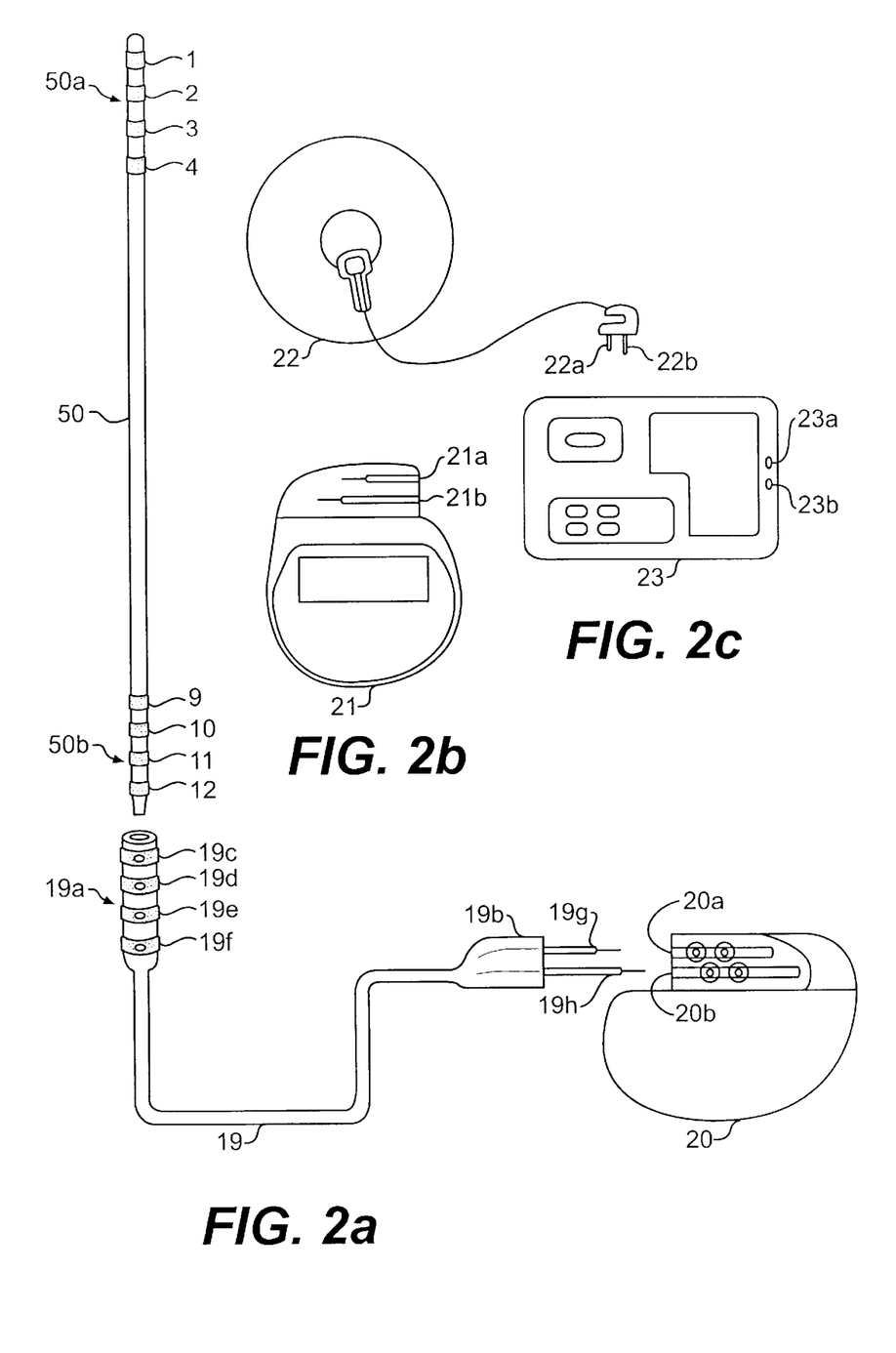
FIG. 2 illustrates schematically the spinal cord stimulation system used in the inventive method.

FIG. 2 illustrates in schematic the basic elements of the spinal cord stimulation system. Lead 50 comprises distal end 50*a* and proximal end 50*b*. Lead extension connector 19 is comprised of a distal end 19*a* and a proximal end 19*b*. Lead extension connector 19 is fitted to the proximal end 50*b* of lead 50 through the distal end 19*a* of the lead extension connector 19. This connection is made with tube conducting terminal connections 9, 10, 11 and 12 at the proximal end 50*b* of lead 50 fitting inside and surrounded by corresponding circular terminal connections 19*c*, 19*d*, 19*e*, and 19*f* on the distal extension connector. Distal extension connector terminals 19*c*, 19*d*, 19*e* and 19*f* contain tightening screws which are fastened using an alien wrench tool provided by the manufacturer. Each of terminal connections 19*c*, 19*d*, 19*e* and 19*f* connects to the corresponding tube conducting terminal connections of the proximal lead 9, 10, 11 and 12 and each in turn corresponds to a distal external conducting electrode 1, 2, 3 and 4 in the distal lead. For example, terminal connection 19*c* is connected to tube conducting terminal connection 9 which is in turn connected to distal external conducting electrode 1.

The proximal end 19*b* of the lead extension connector 19 terminates in prong connectors 19*g* and 19*h* which fit into the source of energy transmission 20 (in this case an internal power source generator such as Medtronic 7425 Itrel 3). Prong 19*g* and 19*h* fit snugly into receptacle outlets 20*a* and 20*b* within the energy source. Prong connectors 19*g* and 19*h* are tightened with two external screws per prong connector or energy source receptacles using an allen wrench tool provided by the manufacturer.

Several possible sources of energy transmission are also illustrated in FIG. 2. The decision for which energy source is optimum for each individual patient is based on the energy needs and coverage area. In use, implanted systems especially those running multiple leads, use larger amounts of energy and subsequently the internal generator battery must be replaced more frequently. External radiofrequency energy sources transmitted through antennae to internal implanted receivers have the ability to run multiple lead systems, and can run multiple channels as well, i.e., two separate leads can receive two separate programs. A totally implanted energy source generator with the capability for multiple channels (i.e. different programs for different leads) may also be used.

A totally implantable internalized generator 20 is shown in FIG. 2. An energy system with internalized receiver 21 which has input for the proximal end of the lead extension similar to 19*b* is also illustrated. In this embodiment, energy is transmitted through an externally placed antenna 22 with impulses transmitted through the skin of the patient to the receiver 21. When the energy source is an external transmitter 23, electrical impulses are transmitted from 23 through the antenna 22 through the skin to the internalized receiver 21 through the lead extension connector 19 to the spinal cord stimulator lead proximal end 50b and finally to the distal end 50a where stimulation is transmitted to the spinal cord. Implanted receiver 21 is inserted into and enclosed by the human body in identical fashion as the implanted generator 20 (assuming compatible component lead or leads and lead extension connector(s)). In this embodiment, compatible proximal lead extension connector 19b is inserted into receiver 21 which is implanted under the skin. The connection is made by inserting compatible prong connectors 19g and 19h into compatible inlets 21a and 21b respectively. Antenna 22 is then placed on the skin externally, overlying the implanted receiver 21 and is connected to the external generator 23. The connection is made by inserting compatible antenna prong connectors 22a and 22b into external generator inlets 23a and 23b respectively. In operation, radiofrequency energy is transmitted from external generator 23 through the antenna 22 into the internalized receiver 21. Radiofrequency signals are converted to electrical energy and transmitted through compatible lead extension connector 19 into the lead 50 which stimulates the neural structures underneath.

A number of issues must be addressed in selecting the best stimulation system for a particular patient. The first decision is whether to place a percutaneous or surgical lead for trial and/or permanent implantation. Percutaneous leads are advantageous in that they are less invasive to place, but they tend to cover a smaller area of stimulation and are more likely to migrate. These problems can be overcome with the placement of multiple lead systems with more electrodes for stimulation as well as dual channel systems which provide versatility in programming or with surgical leads for permanent implantation. The second decision which must be made is whether to use an internal or an external power source. Internal power sources are less cumbersome to the patient, but are more likely to need replacement for battery life at high output and are not currently capable of providing dual or multi-channel stimulation. The third decision involves the appropriate selection of the number of leads placed and the number of electrodes per lead. As mentioned, multiple leads with multiple channels and multiple electrodes can overcome problems with coverage area and migration and can enable transverse stimulation with dual channel systems. Finally, single or multichannel systems must be chosen. Any system may be a viable option to provide stimulation for smoking cessation, with some possible advantages with certain systems (see preferred embodiment).

Patient Screening

Before using spinal cord stimulation for smoking cessation, the appropriateness of the therapy must be determined for each patient. This determination includes the patient presenting with a history of smoking refractory to other methods (i.e. prior relapse following attempted cessation). A psychological interview (similar to those conducted for pain management by spinal cord stimulation) is also necessary to evaluate the patient's psychological status and to prepare them for the implantation of foreign material. The interview should include the administration of an MMPI (Minnesota Multiphasic Psychological Inventory) which measures ten scales including hypochondriasis, depression, conversion/hysteria, psychopathic deviate, masculinity, femininity, paranoia, psychastenia, schizophrenia, hypomania, and social introversion. The MMPI also includes validity scales which test for consistency in answering. The MMPI is the gold standard of psychological tests and is the most frequently used test for patient screening prior to spinal cord stimulation. In addition, the 90-R symptom checklist is a fast and easy test measuring somatization, depression, anxiety, anger, and paranoia. The Beck Depression Inventory, Spielburg State Trait Anxiety Inventory, Chronic Illness Problem Inventory and Oswestry Disability Questionnaire may also be used in addition to the psychological interview. The Fagerstrom Tolerance Questionnaire and the Fagerstrom Test for Nicotine Dependence may be used to assess degree of nicotine dependence. Suggested exclusion criteria for implantable technology (as with pain management) include active psychosis, measured uncontrolled depression or anxiety, active suicidal behavior, active homicidal behavior, and serious cognitive deficits such as those found in dementia or severe sleep disturbances.

Spinal Stimulation Trial

Before using the method, the patient will first undergo a screening trial of spinal cord stimulation to determine if the patient is a suitable candidate for this procedure. The screening trial comprises percutaneous placement through an epidural needle of a temporary trial lead into the epidural space overlying the dura and spinal cord. Trial screening may also be performed through surgical incision but this method of placement is an overly extensive procedure in the event of a failed trial. The screening trial may also include the implantation of multiple leads with multiple electrodes. Leads may be placed along the spinal cord axis (parallel to the spinal cord), oblique to the spinal cord axis, or transverse to the spinal cord axis according to methods well know in the art of pain management.

In the screening trial, the patient is first taken into the operating room and placed prone on the operating room table. Using fluoroscopic guidance, the spinal levels are identified. The patient is prepped and draped in sterile fashion. The needle is inserted percutaneously into the epidural space using fluoroscopic guidance as well as the loss of resistance technique or whatever method was previously used for epidural needle placement. The spinal cord stimulator lead is passed under fluoroscopic guidance into the epidural space overlying the spinal cord until the desired position is achieved.

Figure 3A:
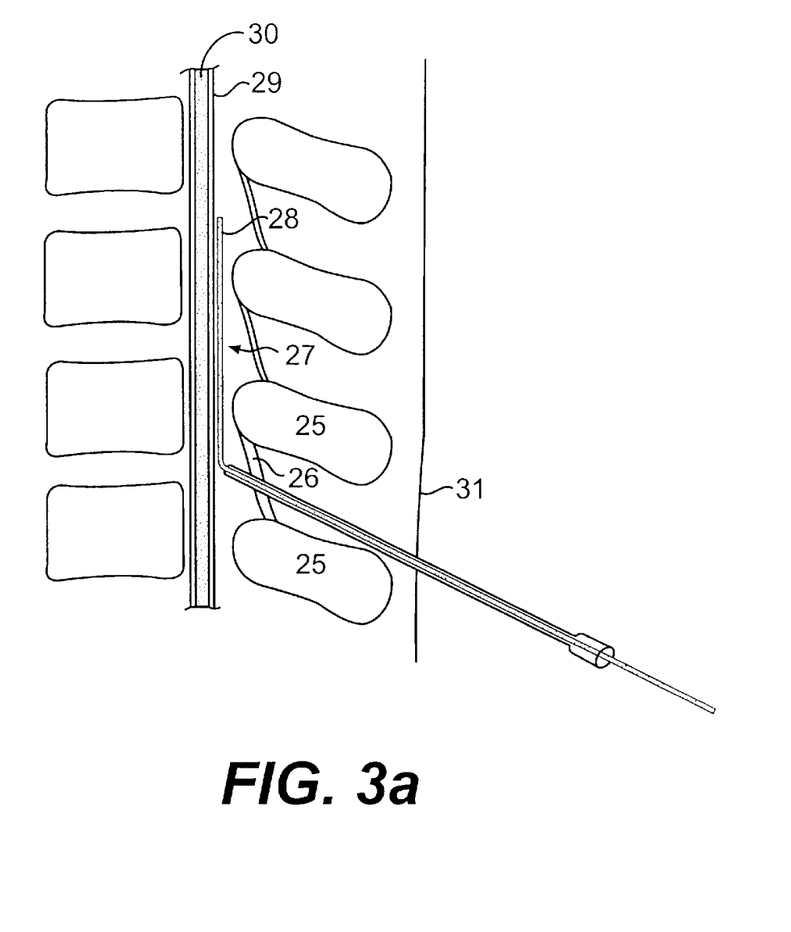
FIGS. 3a and 3b illustrate a side view of lead placement in the inventive method and an anterior posterior view of lead placement in the inventive method respectively.
Figure 3B:
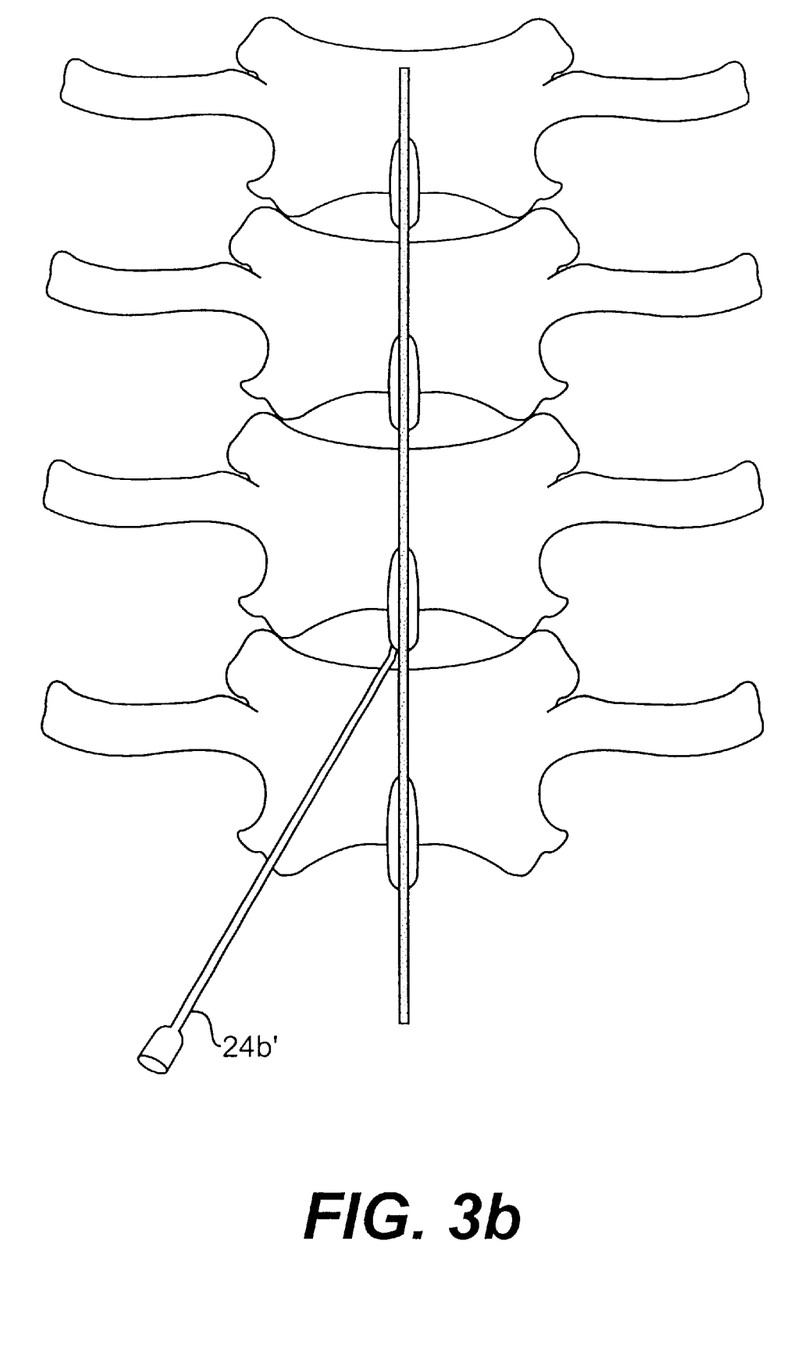

FIG. 3a illustrates epidural needle 24 inserted between spinous processes 25 and passing through ligamentum flavum 26 into the epidural space 27. The distal position of the lead in the cord is identified as 28. The distal lead electrodes overlie the dura 29 and the spinal cord 30. The needle passes through skin 31. FIG. 3a illustrates the lead placement in the side or sagittal view. The anterior posterior view in FIG. 3b illustrates the epidural needle placed at the midline 24b or in paramedian fashion 24b'.

Figure 4A:
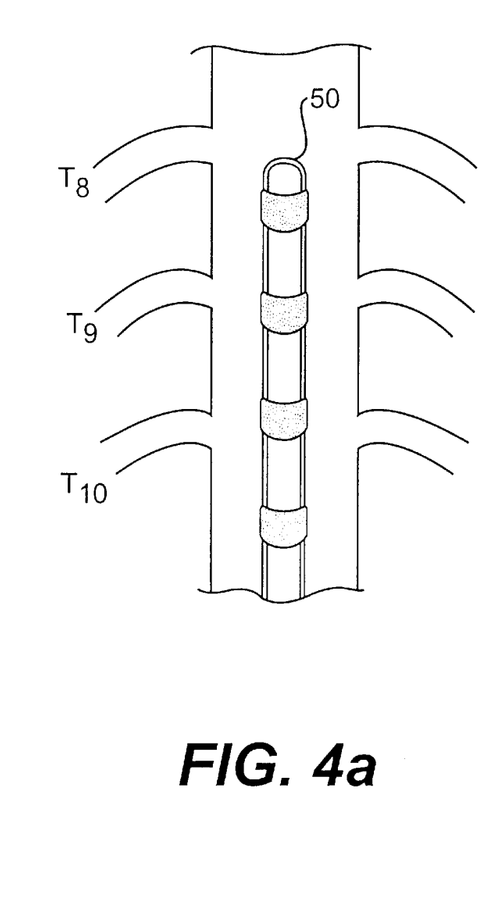
FIG. 4a illustrates a single lead in a midline thoracic placement according to the inventive method.
Figure 4B:
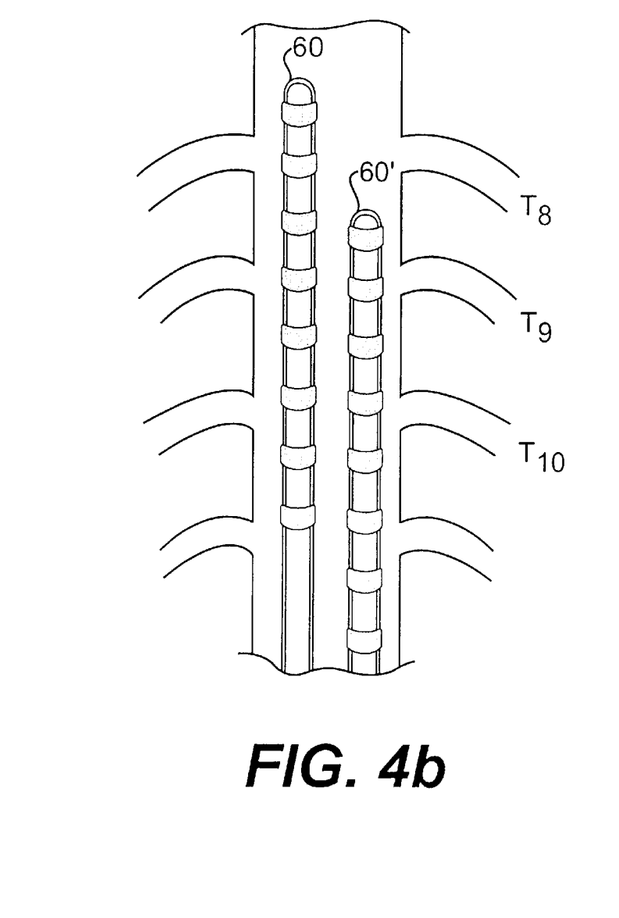
FIG. 4b illustrates the placement of a multiple electrode array system in a thoracic placement according to the inventive method.

FIG. 4a illustrates a lead 50 placed at the midline of the spinal cord with the tip at the level of the eighth thoracic vertebral level T8. In FIG. 4b, two eight-electrode leads 60 and 60' are both placed in the spinal cord with lead 60 passed the eighth thoracic vertebral level T8 and 60' passed the ninth thoracic vertebral level T9. This configuration could also be achieved with 2 four electrode leads or a combination. Leads 60 and 60' may be connected to the same or separate power sources and receive identical or individual programs from the same or different power sources. The two eight-electrode leads 60 and 60' placed in the spinal cord represent an example of a multi-electrode array system.

After placement in the spinal cord, the trial lead or leads are connected to an external generator power source via a lead extension connector 19 which is disposable. Variations in amplitude are administered from 0 to 15 volts, variations in pulse width from 0–450 µs, variations in rate from 0–150 cps (Hz) and variations in electrode polarity (i.e. positive/negative polarity in the first, second, third, fourth, fifth, sixth, seventh, etc., conducting electrodes). The stimulation trial begins with basic settings in polarity with the second most distal lead negative and the third most distal lead positive with a rate of 80 and a pulse width of 270. The amplitude is slowly increased from 0 volts until stimulation is detected by the patient. Amplitude requirements are highly variable and depend on both the position of the lead or leads and the contact quality.

Stimulation is detectable when the patient experiences tingling in areas of skin in the back and lower extremities in the case of a thoracic or lumbar spinal cord stimulation, in the areas of skin in the abdomen and chest wall with upper thoracic stimulation or in the areas of skin in the upper extremity and upper chest wall in the case of cervical spinal stimulation. To ensure the lead is placed along the dorsum of the spinal cord (and thus stimulating the dorsal horn), the sensory feeling of tingling is preferable over the motor feeling of pulling or muscle twitching. Dorsal placement may also be verified fluoroscopically. The lead may be superficially fastened to the skin (e.g., with a single suture and sterile barrier dressing) for easy removal at the end of the trial. Alternatively, the lead may be partially internalized. The latter procedure involves extending the needle puncture site into a small incision, anchoring the lead to the spinous ligaments with suture and tunnelling a temporary lead extension connector to a distal exit site. The partial internalization procedure preserves the lead for permanent use (the temporary connector is discarded) but requires a more extensive removal procedure in the event of a failed trial.

The screening trial may extend from about 3 to about 10 days or more with frequent evaluation of smoking habits. The evaluations will comprise subjective reports from the patient of smoking craving and a tally of the number of cigarettes smoked. The evaluations may also include objective evidence such as biochemical markers, preferably exhaled CO or saliva cotinine. At the end of the screening trial, a decision on whether on not to permanently implant the lead will be made based on criteria for success. These criteria will include significant diminution of craving, significant decreased intake of cigarettes (less than 50% intake of prior habit) and minimal or no withdrawal symptoms. Withdrawal symptoms may be subjective and compared to previous quitting attempts and interventions used. If the screening trial is considered successful, then the patient will proceed with permanent implantation of the spinal cord stimulator system. Permanent implantation may include removal of the trial screening lead (or leads) and subsequent re-implantation of a new spinal cord stimulator lead (or leads), power source and internal lead extension connector. Or the permanent implantation procedure may include internalization of the trial screening lead (or leads) if this lead (or leads) was anchored and tunneled (i.e. partially internalized to remain sterile) during the trial.

Permanent implantation of the spinal cord stimulator lead or leads after a successful screening trial comprises the placement of a permanent spinal cord stimulator lead or leads (similar or identical to the trial lead if percutaneously placed, paddle lead if placed through laminotomy). Placement of the permanent lead or leads is performed by the same method used for implantation of the trial screening lead (if percutaneous not laminotomy). In the permanent implantation procedure, the patient is taken to the operating room and placed in the prone position with fluoroscopic guidance as described for the screening trial procedure. The spinal level selected is similar but not necessarily identical to the trial screening level in the sacral, lumbar, thoracic or cervical areas. A spinal cord stimulator lead or leads are placed as described for the screening trial procedure. Once stimulation reproduces the stimulation observed with the trial lead or leads, the percutaneous insertion sites are extended as an incision using a scalpel to include the sterile lead extension connector pocket. Alternatively, laminotomy or laminectomy may be performed with placement of a surgical lead. A distal site is selected for permanent generator or receiver implantation and a tunnel is made from the midline incision (where lead placement occurs) to the distal pocket site for the energy source.

Figure 5:
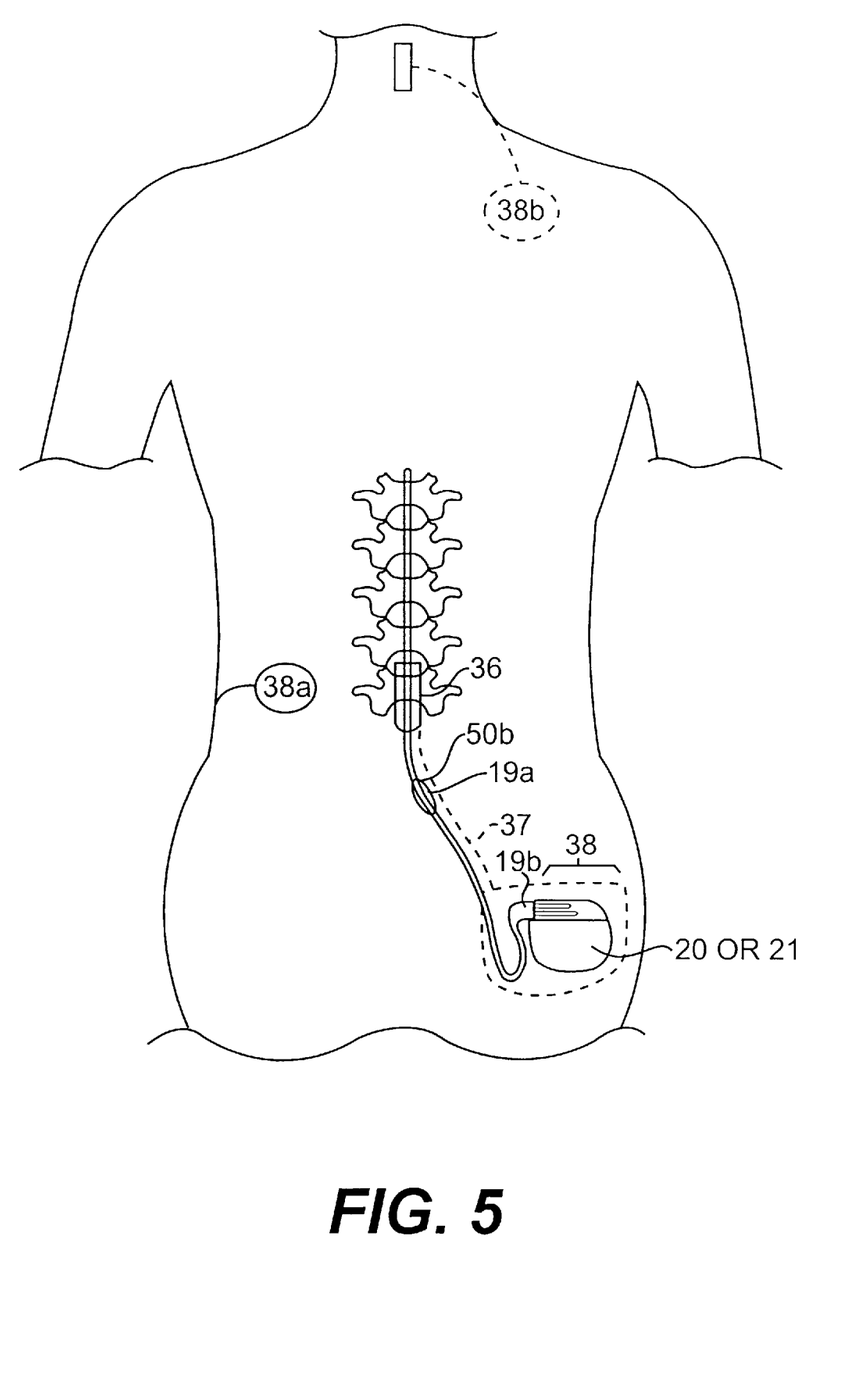
FIG. 5 illustrates a permanent implantation of the spinal cord stimulation system used according to the inventive method.

As illustrated in FIG. 5, the lead extension connectors pass through the tunnel to form a connection between the proximal end of the spinal cord stimulator lead and the power source generator or receiver as described previously. The proximal end of spinal cord stimulator permanent lead 50b extends from a midline incision 36. A tunnel 37 is made from the midline incision 36 to a distal pocket site commonly made in the upper buttocks 38, in the anterior abdomen 38a or the upper chest 38b in cervical stimulation. Lead extension connector distal connector site 19a is connected to the proximal end of the spinal cord stimulator lead 50b and the proximal end of the lead extension connector 19b is connected to the internal energy source (or receiver) 20 (or 21) which lies in the distal pocket.

Connections are made at the midline site between the spinal cord stimulator lead or leads and the lead extension connector(s). Connections are also made between the lead extension connector or connectors and the receiver generator or generators as power source. Electrical stimulus is now provided with an internal system after closure of the midline incision and distal pocket site or sites. This system is now internalized and will reproduce the successful results of the trial period. Changes in generator settings are performed by telemetry using an external compatible programmer. Alternatively, an implanted receiver with external power source transmitted to the receiver via an external antenna may be used for the permanent implantation. In this system, the receiver is implanted identically to the internal generator and is connected to the lead extension connector which connects to the lead. In this manner an external power source transmits electrical stimulation power through the antenna to the internal receiver which transmits the energy into the lead. The advantage of this system is primarily prolonged life as batteries are easily changed in the external system and therefore can be practically used for higher energy levels.

In a permanent implantation, the implanted lead or leads may remain in place for a time period between about one month to about ten years. Shorter time periods are also possible. For example, the implanted lead or leads may remain in place for a time period between about one year to about five years. The time period of implantation may also extend between about one year to about two years.

The patient is followed up immediately post-implantation according to standards for routine post-operative care and wound checks (approximately two times per week for the first week). The target quit date for smoking is set as the day of implantation. To monitor the treatment, the patient keeps a diary to record cigarette intake as well as withdrawal symptoms. Symptoms of nicotine withdrawal include craving for cigarettes, depressed mood, insomnia, irritability, anger, anxiety, difficulty concentrating and increased appetite. The patient is seen twice a week for the first week, once per week for the next seven weeks and then once per month through the end of the first year. The success of the treatment is defined as greater than 50% reduction in the number of cigarettes smoked per day sustained to six months post quit date followed by complete cessation of smoking at the one year mark and sustained for a period of six months. Success criteria are evidenced by the patient report of cigarette number verified by concurrent reduction/elimination of exhaled carbon monoxide and saliva cotinine. Side effects should decrease over the course of the first year and are expected to be minimal by the end of that year.

Stimulation may also be terminated for a time period between about one day to about six months to evaluate the possibility of explantation of the lead or leads. Other time periods may be used for this evaluation, including a time period between about two weeks to about three months and a time period between about one month to about two months.

The inventive method for treating addiction to tobacco products is nondestructive and reversible, does not involve any pharmacologic agents and its use of a trial screening period predicts the success of permanent implantation. An attractive feature of the inventive method is its ability to be integrated into combinations with other therapies currently in use for smoking cessation. Although marginally successful, combination therapies have still shown the best success in achieving smoking cessation. The combination of spinal cord stimulation with pharmacologic therapy (both nicotine and non-nicotine) and behavioral programs is the preferred combination and should significantly increase the success of what have here-to-now been historically unsuccessful programs. Spinal cord stimulation may also be combined with pharmacologic therapy alone or with behavioral programs alone. Multicomponent behavioral programs contemplated for combination with spinal stimulation alone in combination with pharmacologic therapy include aversive techniques, coping strategies and relapse prevention. Pharmacologic treatments contemplated for combination with spinal cord stimulation alone or in combination with behavioral programs include antidepressant medication (e.g., bupropion) as well as nicotine replacement therapy using gum, patches or lozenges. Nicotine fading may also be used. By combining various therapies, physiologic dependence on nicotine should be maximally reduced since its withdrawal would be tolerated physically and behavioral problems would be addressed to improve patient coping and prevent relapse.

Given the variety of available leads, lead systems, power sources and procedural combinations, many approaches are possible and viable for use in treatment of tobacco addiction. However, the approach with the most advantages (and thus the preferred embodiment) is as follows.

Patient eligibility is designated by initial criteria of need combined with psychological testing and evaluation as described above. A percutaneous trial is preferably performed with one or two four-electrode (quadripolar) leads placed through an epidural needle. Most preferably, two leads are employed in the trial. The leads are not tunneled but are externalized to external lead extension connectors and a screening power source. Insertion of the leads are in the low thoracic or high lumbar region and the leads are placed to the area of the sixth to tenth thoracic vertebrae. Dual channel stimulation is performed for the trial which allows individual programs to be used for each lead. This combination also allows for the most versatility in setting combinations as well as "cross talk" (transverse stimulation) between individually programmed leads.

In the preferred embodiment, the trial period lasts from seven to ten days with evaluation visits on the third, sixth and tenth day of the trial. Success is assessed by determining the extent to which the patient's nicotine dependence has been suppressed or extinguished. One way to monitor the patient's progress is by observing the number of cigarettes smoked per day before and after the trial. The exhaled carbon monoxide and saliva biochemistry (cotinine) levels maintained by the patient before and after the trial may also be used to monitor the success of the procedure. Trial leads are removed around the tenth day and if success parameters are met, permanent implantation is scheduled. Permanent implantation consists of similar lead placement compared to the trial leads with two quadripolar leads placed. The preferred power source is an external power source transmitting radiofrequency energy through an antenna to an internal receiver. The advantage of this approach is that the patient is spared a surgical procedure with percutaneous trial and lead removal and subsequent permanent implantation is minimally invasive. In addition, the two lead system gives the most versatility in parameters as well as in broad-based coverage and the duality of leads can compensate for lead migration. Finally, the advantage of an external power source enables not only dual channel (lead individuality in programming), but also enables the use of higher power levels without concern for battery rundown. Based on the following case report, energy levels may be higher and coverage area needed more broad than that needed for pain management.

Improvements of the device and method may include the use of multiple lead types, electrode numbers, multi-channel leads placed, paddle leads, multiple generator input of multiple leads for single generator, multiple generators, implanted receivers with external power sources connected to single or multiple leads with various number of electrodes. Settings for these leads may be identical as when inserted into single generator power source or may be independent of each other. There can be transmission from one lead electrode to another electrode on the same lead or there can be transmission from lead electrode or electrodes on a single lead to electrodes on a different lead or to multiple other leads.

Computer programs may also be used to program a complex network for transmission between multiple leads and multiple-lead electrodes for the maximum transmission into and through the spinal cord. This can be performed at multiple levels including low lumber up to high cervical with most likely positive results being in the mid to low thoracic area. Electrode polarities from distal to most proximal two electrode, four electrode, eight electrode, and even higher electrode numbered systems can vary polarity positive to negative in each of the two, four, eight, sixteen electrodes with all permutations of positive and negative included. Any electrode on a given lead can transmit and communicate to any electrode on a separate lead in combination with polarity changes and multiple permutations. Besides electrode polarity, placement of single or separate leads in addition to covering all levels of the spinal cord may comprise two or more separate locations within the spinal cord. For example, one lead may be placed low lumbar with another lead placed thoracic with communication between the two leads or independent stimulation between the two leads. Paddle lead systems may be inserted through laminotomies or percutaneously (if feature variations are made), and these may be used independently, with multiple paddle leads or with combinations of percutaneous leads.

As note above, the settings for electrical stimulation include amplitude, rate and pulse width along with polarity of contact electrodes. Additionally, the current art for spinal cord stimulation includes continuous mode stimulation or cycling mode stimulation. Continuous mode stimulates continuously and may be required long-term for optimal results. Cycling mode stimulation is available in cycles which automatically stimulates on and off times in varying durations. This can significantly increase the battery life in totally implanted systems. In addition to continuous and cycling modes, biphasic stimulation is available which allows electrode polarity to reverse with every pulse. The previously mentioned are part of cycling modes. Single stimulation, dual stimulation and multiple electrode stimulation arrays are also available. This allows stimulation of single lead of 4, 8 or 16 electrodes (projected greater number of electrode leads to become available). Dual stimulation provides different stimulation programs for separate channels for the generator power source to two sets of electrodes (two four-electrode leads, two eight-electrode leads), or differing stimulation to the two sets of four electrodes or two sets of eight-electrode leads. Pulse width, amplitude and rate are the same for both channels. Future variations will provide versatility in multiple lead systems of any electrode number.

Application of the inventive method is illustrated with the example set forth below. In this case, the patient required a high degree of stimulation as evidenced by the significant feelings of tingling and stimulation in his legs combined with a subjective feeling of motor weakness. This may represent the required level of stimulation for smoking cessation or could indicate this particular patient to be one of a difficult population.

EXAMPLE 1

A 48 year-old male presented with a greater than ten year history of severe chronic lower back and leg pain status post extensive lumbar spinal surgery with laminectomy and fusion but continued pain in his low back and bilateral legs. The pain did not follow any dermatomal distribution indicating discrete nerve root involvement. Rather his symptoms were consistent with arachnoiditis with lower extremity radiculitis.

The patient was refractory to multiple interventions, both psychological, physical, pharmacological and procedural. These included local injections in the muscle and fascia, epidural injections, nerve root injections, external electrical stimulation (transcutaneous electrical nerve stimulation), lumbar facet injections, injection at the fusion site, cryoneurablation, high dose chronic opiate therapy, physical therapy of all types, and psychological pain management techniques. The patient was considered to be a good candidate for spinal cord stimulation applying prior art spinal cord stimulation for pain management.

The patient was taken to the operating room and lay prone on the operating room table and subsequently underwent placement of a trial screening spinal cord stimulator electrode. This involved insertion into the spinal interspace at T12-L1 and insertion of a percutaneous four-electrode system lead into the epidural space. The lead was advanced until the distal tip lay at the level of T8 at the midline. The proximal end was connected to an external power source and manipulated until the patient could feel tingling (stimulation) in both of his legs. The lead was secured at its percutaneous insertion site with #3.0 silk and an occlusive dressing. The patient was discharged home with an external power source, Medtronic's external power source Model No. 3625 with variations available for amplitude, pulse width and rate. The patient's electrode polarity was electrode 0 most distal electrode as the positive pole and electrode 2 the third most distal electrode as the negative electrode. Amplitude ranged 2.5–8.0 during the trial period with a pulse width of 300 (range 100–450) and a rate of 50 (range 25–120). The patient underwent a one-week trial period with the implanted lead during which time he was seen three times in the outpatient clinic.

The patient reported only a mild decrease of his pain symptoms during the first clinic visit. At this point, electrode polarities were changed to include 0 positive, 2 negative, 3 positive. The patient reported that he felt strong stimulation in his legs to the point where he may have been experiencing some motor component and weakness in his legs. Strength was normal by gross motor testing and he was able to walk without assistance. The patient was seen twice more during the trial period. At the end of a one-week trial period, the patient reported that his pain symptoms were decreased in both of his legs but unfortunately his low back pain was only marginally affected. This report of pain relief resulted in the assessment that less than 50% of the patient's total pain symptoms were decreased by spinal cord stimulation and he thus failed the screening trial for permanent implantation based on pain management.

However, the patient made a notable observation which he reported at the end of the trial. The patient self-reported a heavy smoking habit of many years duration (two packs per day for greater than 25 years) but observed that he had no craving to smoke cigarettes during the entire trial. The patient reported that on the third day of the trial, he realized that he had not thought about smoking a cigarette for three days. The patient further reported that he had not smoked any cigarette for the entire duration of the trial nor did he note any significant withdrawal symptoms. The patient reported simply that he had "forgotten all about having to smoke". The patient also observed that he had made many previous unsuccessful efforts to quit smoking using conventional interventions such as nicotine containing gum. However, upon removal of the trial lead, the patient reported that his cravings returned in one day after spinal cord stimulation was discontinued.

While the invention has been illustrated and described in detail in the drawings and foregoing descriptions, the same is to be considered illustrative and not restrictive in character. All changes and modifications that come within the spirit of the invention are contemplated as within the scope of the invention.

If the inventive method is used to suppress craving for other chemical substances such as alcohol, the target quit date is again selected as the day of implantation. To monitor the treatment, the patient keeps a diary to record substance intake and any withdrawal symptoms specific to the chemical substance. Success criteria are chose to be compatible with established success criteria for that chemical substance.

What is claimed is:

1. A method for suppressing chemical substance craving comprising the steps of:
   (a) implanting a lead comprised of at least two electrodes into the epidural space of a human body overlying the spinal cord;
   (b) connecting the lead to a lead extension connector;
   (c) connecting the lead extension connector to a power source capable of generating electrical power; and
   (d) varying at least one of the characteristics of the electrical power generated by the power source for a time period sufficient to suppress the chemical substance dependence of the patient.

2. The method of claim 1 wherein the chemical substance is nicotine and the polarity of the electrodes is varied at the same time as at least one of the characteristics of the electrical power.

3. The method of claim 2 wherein variation of the polarity of the electrodes is achieved by activating at least two electrodes per lead up to the maximum number of electrodes contained on the lead.

4. The method of claim 3 wherein the number of electrodes activated per lead ranges from at least two up to eight electrodes per lead.

5. The method of claim 3 wherein the number of electrodes activated per lead ranges from at least two up to four electrodes per lead.

6. The method of claim 3 wherein three electrodes are activated per lead.

7. The method of claim 2 wherein one of the characteristics of electrical power that is varied is the amplitude.

8. The method of claim 7 wherein amplitude is varied between about 0 volts to about 15 volts and wherein the voltage chosen is as high as can be tolerated by the patient so as to achieve maximum stimulation.

9. The method of claim 7 wherein amplitude is varied between about 0.1 volts to about 8 volts and wherein the voltage chosen is as high as can be tolerated by the patient so as to achieve maximum stimulation.

10. The method of claim 7 wherein amplitude is varied between about 1 volts to about 6 volts and wherein the voltage chosen is as high as can be tolerated by the patient so as to achieve maximum stimulation.

11. The method of claim 7 wherein amplitude is varied between about 1 volts to about 4 volts and wherein the voltage chosen is as high as can be tolerated by the patient so as to achieve maximum stimulation.

12. The method of claim 2 wherein one of the characteristics of electrical power that is varied is the pulse width.

13. The method of claim 12 wherein the pulse width is from about 0 to about 450 microseconds.

14. The method of claim 12 wherein the pulse width is from about 180 to about 270 microseconds.

15. The method of claim 12 wherein the pulse width is from about 240 to about 270 microseconds.

16. The method of claim 2 wherein one of the characteristics of electrical power that is varied is the rate.

17. The method of claim 16 wherein the rate is from about 0 to about 150 cps.

18. The method of claim 16 wherein the rate is from about 25 to about 80 cps.

19. The method of claim 16 wherein the rate is from about 50 to about 80 cps.

20. The method of claim 2 wherein the number of leads implanted into the spinal cord ranges from 1 lead to 10 leads.

21. The method of claim 20 wherein the number of leads implanted into the spinal cord ranges from 1 lead to 4 leads.

22. The method of claim 20 wherein the number of leads implanted into the spinal cord ranges from 1 lead to 2 leads.

23. The method claim 20 wherein the number of leads implanted into the spinal cord is 2.

24. The method of claim 20 wherein the number of electrodes per lead ranges from between 2 to 16 per lead and wherein the number or electrodes per lead is the same or different.

25. The method of claim 20 wherein the number of electrodes per lead ranges from between 4 to 8 per lead.

26. The method of claim 20 wherein the number of electrodes per lead is 4.

27. The method of claim 20 wherein the lead or leads are placed percutaneously.

28. The method of claim 20 wherein the lead or leads are placed surgically.

29. The method of claim 20 wherein the lead or leads are implanted so as to range from the sacral position to the high cervical position in the spinal cord.

30. The method of claim 20 wherein the lead or leads are implanted from the upper lumbar to the lower cervical position in the spinal cord.

31. The method of claim 20 wherein the lead or leads are implanted from the lower thoracic to the higher thoracic position in the spinal cord.

32. The method of claim 20 wherein the lead or leads are implanted from the lower thoracic to the middle thoracic position in the spinal cord.

33. The method of claim 20 wherein computer programming is employed to enable communication between the lead or leads and the lead or lead electrodes to provide a plurality of possible combinations with multiple leads and lead electrodes.

34. The method of claim 29 wherein the lead or leads are positioned so that the lead or leads are parallel to the midline of the spinal cord and wherein the lead or leads are to the right of the midline.

35. The method of claim 29 wherein the lead or leads are positioned so that the lead or leads are parallel to the midline of the spinal cord and wherein the lead or leads are to the left of the midline.

36. The method of claim 29 wherein the lead or leads are positioned so that the lead or leads are parallel to the midline of the spinal cord and wherein the lead or leads are directly on the midline.

37. The method of claim 29 wherein more than one lead is implanted so that the leads are positioned to the right and left of the midline of the spinal cord.

38. The method of claim 29 wherein the lead or leads are positioned oblique to the midline.

39. The method of claim 29 wherein the lead or leads are positioned transverse to the midline.

40. The method of claim 2 comprising the additional step of treatment with a combination therapy.

41. The method of claim 2 comprising the additional step of treatment with a pharmacologic therapy.

42. The method of claim 2 comprising the additional step of treatment with a behavioral therapy.

43. The method of claim 1 wherein the chemical substance is nicotine.

44. The method of claim 1 wherein the chemical substance is alcohol.

45. The method of claim 1 wherein the chemical substance is a narcotic.

46. The method of claim 1 wherein the chemical substance is an amphetamine.

47. The method of claim 1 wherein the power source means is located external to the human body.

48. The method of claim 1 wherein the power source means is located in an internal portion of the human body.

49. The method of claim 1 wherein the implanted lead or leads remain in place for a time period between about 1 month to about 10 years.

50. The method of claim 1 wherein the implanted lead or leads remain in place for a time period between about 1 year to about 5 years.

51. The method of claim 1 wherein the implanted lead or leads remain in place for a time period between about 1 year to about 2 years.

52. The method of claim 1 comprising the additional step of terminating stimulation for a time period between about 1 day to about 6 months to evaluate the possibility of explantation of the lead.

53. The method of claim 1 comprising the additional step of terminating stimulation for a time period between about 2 weeks to about 3 months to evaluate the possibility of explantation of the lead.

54. The method of claim 1 comprising the additional step of terminating stimulation for a time period between about 1 month to about 2 months to evaluate the possibility of explantation of the lead.

55. A method for suppressing chemical substance craving comprising the steps of:
   (a) implanting one or more leads comprised of at least two electrodes into the epidural space of a human body overlying the spinal cord in the sacral to high cervical position;
   (b) connecting the lead to a lead extension connector;
   (c) connecting the lead extension connector to a power source capable of generating electrical power; and varying the amplitude of the electrical power from between about 0 to about 15 volts, varying the pulse width of the electrical power from about 0 to about 450 microseconds and varying the rate of the electrical power from about 0 to about 150 cps for a time period sufficient to suppress the chemical substance dependence of the patient.

56. The method of claim 55 wherein the chemical substance is nicotine.

57. A method for suppressing nicotine craving comprising the steps of:
   (a) implanting two leads comprised of between four to eight electrodes each into the epidural space of a human body overlying the spinal cord in the throracic region;
   (b) connecting the lead to a lead extension connector;
   (c) connecting the lead extension connector to an internal receiver capable or receiving power from an external source and transmitting said power as electrical energy to the implanted lead; and
   (d) varying the amplitude of the electrical power from between about 0 to about 4 volts, varying the pulse width of the electrical power from about 240 to about 290 microseconds and varying the rate of the electrical power from about 80 to about 120 cps for a time period sufficient to suppress the nicotine dependence of the patient.

* * * * *